(12) United States Patent
Olovsson

(10) Patent No.: US 10,261,056 B2
(45) Date of Patent: Apr. 16, 2019

(54) METHOD AND VALVE IN CONTINUOUS CHROMATOGRAPHY SYSTEM

(71) Applicant: GE Healthcare Bio-Sciences AB, Uppsala (SE)

(72) Inventor: Bjorn Markus Olovsson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 139 days.

(21) Appl. No.: 15/129,636

(22) PCT Filed: Mar. 16, 2015

(86) PCT No.: PCT/EP2015/055463
§ 371 (c)(1),
(2) Date: Sep. 27, 2016

(87) PCT Pub. No.: WO2015/144481
PCT Pub. Date: Oct. 1, 2015

(65) Prior Publication Data
US 2017/0146495 A1    May 25, 2017

(30) Foreign Application Priority Data
Mar. 28, 2014 (SE) ...................................... 1450357

(51) Int. Cl.
*G01N 30/20* (2006.01)
*B01D 15/18* (2006.01)
(Continued)

(52) U.S. Cl.
CPC ......... *G01N 30/20* (2013.01); *B01D 15/1842* (2013.01); *F16K 11/0743* (2013.01);
(Continued)

(58) Field of Classification Search
None
See application file for complete search history.

(56) References Cited

U.S. PATENT DOCUMENTS 3,747,630 A * 7/1973 Hurrell ................. F16K 11/074
137/312
4,614,204 A    9/1986 Dolejs
(Continued)

FOREIGN PATENT DOCUMENTS

CN    101044346 A    9/2007
CN    101617225 A    12/2009
(Continued)

OTHER PUBLICATIONS

International Search Report and Written Opinion regarding International Application No. PCT/EP2015/055463, dated Aug. 18, 2015, 16 pages.
(Continued)

*Primary Examiner* — Paul M. West
*Assistant Examiner* — Mark A Shabman
(74) *Attorney, Agent, or Firm* — Wood IP LLC

(57) ABSTRACT

A method and a rotary valve in a continuous chromatography system. The rotary valve comprises a stator with an inner stator face, and a rotor with an inner rotor face arranged in sealing contact with the inner stator face. The stator comprises at least a first and a second inlet orifices, at least two first outlet orifices, a second outlet orifice and a third outlet orifice, and the rotor interconnection paths are arranged to:
  in at least one rotary position connect the first inlet orifice to the second outlet orifice and the second inlet orifice to the third outlet orifice, and
  in at least two other rotary positions connect the first inlet orifice with any one of the first outlet orifices at the same time as the second inlet orifice is connected to the second outlet orifice.

8 Claims, 10 Drawing Sheets

(51) Int. Cl.
*F16K 11/074* (2006.01)
*G01N 30/44* (2006.01)
*G01N 30/80* (2006.01)

(52) U.S. Cl.
CPC .............. *G01N 30/44* (2013.01); *G01N 30/80* (2013.01); *G01N 2030/202* (2013.01)

(56) References Cited

U.S. PATENT DOCUMENTS

| | | | |
|---|---|---|---|
| 4,625,569 A | 12/1986 | Toei | |
| 4,632,149 A * | 12/1986 | Oroskar | F16K 11/074 137/625.11 |
| 5,770,088 A | 6/1998 | Ikeda et al. | |
| 6,217,774 B1 | 4/2001 | Nagamatsu | |
| 6,997,213 B1 * | 2/2006 | Towler | B01D 15/1842 137/625.46 |
| 8,017,017 B2 | 9/2011 | Minoda | |
| 8,186,381 B2 | 5/2012 | Wilen | |
| 8,656,955 B2 | 2/2014 | Price | |
| 2003/0098076 A1 | 5/2003 | Nichols | |
| 2004/0129137 A1 * | 7/2004 | Chin | B01D 15/1842 95/108 |
| 2006/0042686 A1 * | 3/2006 | Gamache | F16K 11/074 137/51 |
| 2006/0156792 A1 | 7/2006 | Wang | |
| 2006/0273013 A1 * | 12/2006 | Chin | B01D 15/1842 210/656 |
| 2010/0032603 A1 | 2/2010 | Wilen | |
| 2010/0206812 A1 | 8/2010 | Woods et al. | |
| 2011/0120952 A1 * | 5/2011 | Minoda | B01D 15/1828 210/659 |
| 2012/0125440 A1 | 5/2012 | Price | |
| 2013/0068977 A1 | 3/2013 | Picha et al. | |
| 2016/0313289 A1 | 10/2016 | Olovsson et al. | |

FOREIGN PATENT DOCUMENTS

| | | |
|---|---|---|
| CN | 102143789 A | 8/2011 |
| CN | 102918309 A | 2/2013 |
| CN | 105829884 A | 8/2016 |
| EP | 2319599 A1 | 5/2011 |
| JP | 55097206 A | 7/1980 |
| JP | 61134668 A | 6/1986 |
| JP | 61274240 A | 12/1986 |
| JP | 09206502 A | 8/1997 |
| JP | 2010519484 A | 6/2010 |
| JP | 2013533464 A | 8/2013 |
| WO | 03026772 A2 | 4/2003 |
| WO | 2008/103097 A1 | 8/2008 |
| WO | 2008/140377 A1 | 11/2008 |
| WO | 2010024266 A1 | 3/2010 |
| WO | 2010056189 A1 | 5/2010 |
| WO | 2011146861 A1 | 11/2011 |
| WO | 2013160455 A1 | 10/2013 |

OTHER PUBLICATIONS

International-Type Search Report regarding SE Application No. 1450357-7, dated Oct. 2, 2014, 5 pages.
Chinese Office Action Received for Chinese Patent Application 201580027657.X dated Aug. 1, 2017, 13 Pages. (6 pages Official Copy + 7 pages English Translation).
Chinese Office Action and Search Report Received for Chinese Patent Application 201580027657.X dated Oct. 31, 2018, 14 Pages (7 pages Official Copy + 7 Pages English Translation).
Japan Notice of Preliminary Rejection for Japanese Patent Application No. 2017-501479, dated Jan. 29, 2019, 6 pages.

* cited by examiner

METHOD AND VALVE IN CONTINUOUS CHROMATOGRAPHY SYSTEM

CROSS-REFERENCE TO RELATED APPLICATIONS

This application is a filing under 35 U.S.C. 371 of international application number PCT/EP2015/055463, filed Mar. 16, 2015, which claims priority to SE application number 1450357-7, filed Mar. 28, 2014, the entire disclosures of each of which are hereby incorporated by reference.

FIELD OF THE INVENTION

The present invention relates to methods and valves in continuous chromatography systems.

BACKGROUND

Valves are commonly used in devices that involve the transportation of a fluid. A typical type of valve, for example used in laboratory systems of moderate sizes, is the rotary valve.

Generally, a rotary valve has a stationary body, herein called a stator, which co-operates with a rotating body, herein called a rotor.

The stator is provided with a number of inlet and outlet ports. The ports are via bores in fluid communication with a corresponding set of orifices on an inner stator face. The inner stator face is an inner surface of the stator that is in fluid tight contact with an inner rotor face of the rotor. The rotor is typically formed as a disc and the inner rotor face is pressed against the inner stator face in rotating co-operation. The inner rotor face is provided with one or more grooves which interconnect different orifices depending on the rotary position of the rotor with respect to the stator.

Rotary valves can be designed to withstand high pressures (such as pressures above 25 MPa). They can be made from a range of materials, such as stainless steel, high performance polymeric materials and ceramics.

The number of inlets/outlets as well as the design of grooves in the rotor or the stator reflects the intended use of a specific valve. A common type of multi-purpose valve has one inlet port (typically placed in the rotary axis of the valve) and a number of outlets ports that are placed equidistantly around the inlet port. The rotor has a single, radially extending groove that has one end in the rotary centre, thereby always connecting to the inlet, while the other end connects to any one of the outlets depending on the angular position of the rotor with respect to the stator. Such a valve is useful to direct a flow from the inlet to any of the outlets—one at a time.

In chromatography systems for continuous chromatography, such as simulated moving bed systems usually a large number of valves are used for providing feed and buffer to the different columns in the system in correct order. There is a need for better valve arrangements in such systems.

SUMMARY OF THE INVENTION

One object of the invention is to provide a flexible method for performing continuous chromatography.

A further object of the invention is to provide a rotary valve that can be used for continuous chromatography.

A further object of the invention is to provide a continuous chromatography system with convenient and effective valve arrangement.

This is achieved in a method in a simulated moving bed chromatography system comprising a recirculation flow path in which recirculation fluid from the outlet of one column to the inlet of another column is transferred, said method comprising choosing which one of two flows in the chromatography system that should be recirculated in the recirculation flow path.

This is also achieved in a rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluidic contact with a corresponding valve orifice at the inner stator face and the rotor comprises two or more rotor interconnection paths for selective fluidic interconnection of said valve orifices with respect to the rotor position, wherein the stator comprises at least a first and a second inlet orifices, at least two first outlet orifices, a second outlet orifice and a third outlet orifice, and wherein the rotor interconnection paths are arranged to:
  in at least one rotary position connect the first inlet orifice to the second outlet orifice and the second inlet orifice to the third outlet orifice, and
  in at least two other rotary positions connect the first inlet orifice with any one of the first outlet orifices at the same time as the second inlet orifice is connected to the second outlet orifice.

This is also achieved in a chromatography system comprising at least three chromatography columns, said system further comprising:
  a column inlet rotary valve connected to the inlets of at least three columns in the system and to at least three inflows and
  a column outlet rotary valve connected to the outlets of at least three columns in the system and to at least three outflows, and
  a recirculation flow path in which recirculation fluid from the outlet of one column to the inlet of another column is transferred, wherein said recirculation flow path is connected to the inlets and outlets of the columns through the column inlet and column outlet rotary valves, wherein said system further comprises
  a recirculation rotary valve according to any one of the claims 1-3 connected in the recirculation flow path and to one more of the outflows from the column outlet rotary valve.

Hereby a flexible rotary valve for use in for example a continuous chromatography system such as a simulated moving bed system is provided. A rotary valve is provided where flows can be connected in a suitable way for a continuous chromatography method where both feed and wash can be recirculated.

Furthermore, a chromatography system comprising such a rotary valve is provided. This will give a system with fewer valves and fewer flow connections compared to traditional simulated moving bed chromatography systems.

In one embodiment of the invention at least one of the rotor interconnection paths in the rotary valve is a partly bending groove.

In one embodiment of the invention a first inlet orifice is provided in the centre of the rotary valve and the at least two first outlet orifices are provided around a circle around the first inlet orifice and the second inlet orifice is provided at a radial distance R from the first inlet orifice that is different than the distance where the first outlet orifices are provided and a first interconnection path is provided such that it can connect the first inlet orifice with any one of the first outlet orifices and a second interconnection path is provided partly as a circle with an opening on the same radial distance from the first inlet orifice as the second inlet orifice.

In one embodiment of the invention a first outflow from the column outlet rotary valve in the chromatography system is connected to the second inlet orifice in the recirculation rotary valve and a third outflow from the column outlet rotary valve is connected to the first inlet orifice in the recirculation rotary valve and a second inflow in the chromatography system is connected to the second outlet orifice in the recirculation rotary valve.

In one embodiment of the invention the feed recirculation flow path comprises a detector.

In one embodiment of the invention the method comprises directing two of the outflows from the column outlet rotary valve through the recirculation flow path one at the time.

DETAILED DESCRIPTION OF EMBODIMENTS OF THE INVENTION

Figure 1:
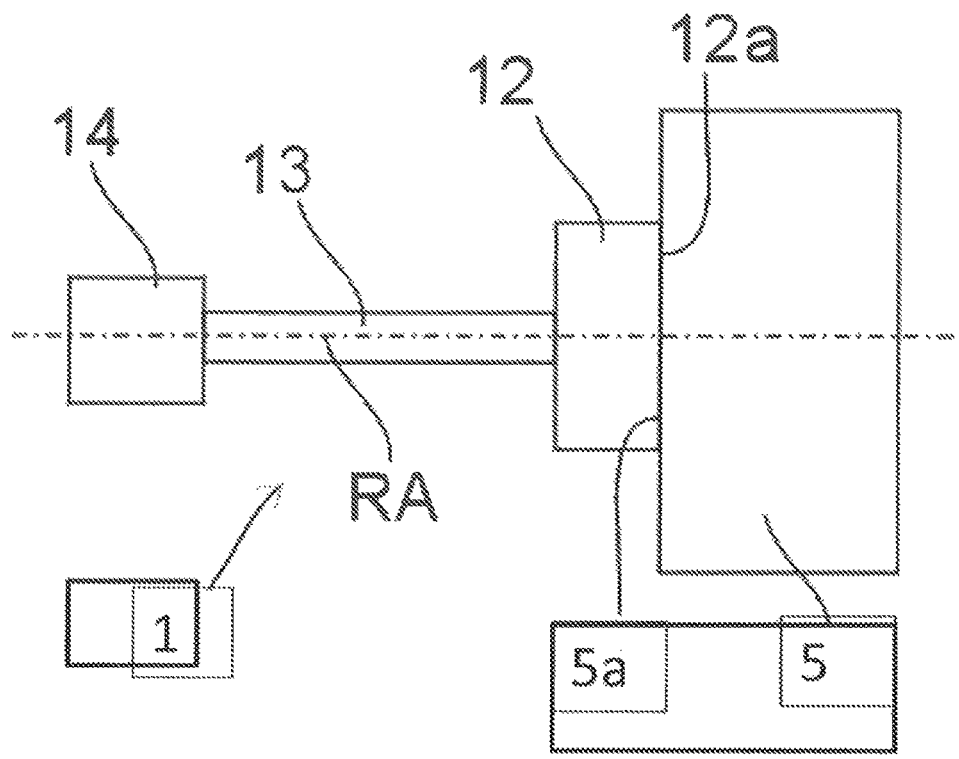
FIG. 1 is a schematic side view of a rotary valve according to one embodiment of the present invention.

The main parts of a typical rotary valve 1 are schematically shown in FIG. 1 (wherein no brackets or similar load carrying or fastening elements are shown). The rotary valve 1 has a stator 5, a rotor 12, a rotary shaft 13 that optionally may be provided with means (not shown) for recognizing its angular position and a driving unit 14 typically comprising a gear box and a motor (although a valve also may be operated manually). The rotor is rotatable with respect to the stator around a rotary axis RA of the valve.

The stator 5, which is fixed with respect to the instrument into which it is built, is provided with ports for fluid communication with a fluid source/outlet and any component with which the valve is to co-operate. The ports may be positioned on any suitable part of the stator, and in any suitable direction. The ports are provided with means to connect capillaries or tubing. Such means may be of any suitable type, such as conventional Valco fittings well known to anyone skilled in the art. The ports are via channels in fluid communication with a corresponding set of valve orifices on an inner stator face 5a, i.e. the surface of the stator that during operation is in contact with the rotor 12.

The rotor 12 is typically formed as a disc and has an inner rotor face 12a that is pressed against the flat inner stator face 5a during operation to achieve sealing contact there between. The inner rotor face 12a is provided with one or more interconnection paths which interconnect different valve orifices of the inner stator face 5a depending on the rotary position of the rotor with respect to the stator. The interconnection paths may be any type of path capable of providing fluidic contact between two valve orifices, and may be comprised of an internal channel with discrete orifices, grooves in the inner rotor face or the like.

According to the invention a method is provided in a simulated moving bed chromatography system comprising a recirculation flow path in which recirculation fluid from the outlet of one column to the inlet of another column is transferred The method comprises choosing which one of two flows in the chromatography system that should be recirculated in the recirculation flow path. This could be accomplished by using the recirculation rotary valve as described below but also by using a set of less complex valves, for example rotary valves, solenoid valves or pneumatic valves.

In one embodiment the chromatography system further comprises at least one column inlet valve connected to the inlets of at least three columns in the system and to at least three inflows and at least one column outlet valve connected to the outlets of at least three columns in the system and to at least three outflows, and a recirculation flow path in which recirculation fluid from the outlet of one column to the inlet of another column is transferred, wherein said recirculation flow path is connected to the inlets and outlets of the columns through the column inlet and column outlet valves. The method of the invention comprises directing two of the outflows from the at least one column outlet valve through the recirculation flow path one at the time. The outflows to be recirculated could be feed outflow and wash as described in relation to the embodiments described below.

The at least one column inlet valve and the at least one column outlet valve could be one inlet rotary valve and one outlet rotary valve as described in the embodiments below or a set of less complex valves, for example less complex rotary valves, solenoid valves or pneumatic valves.

Figure 2A:
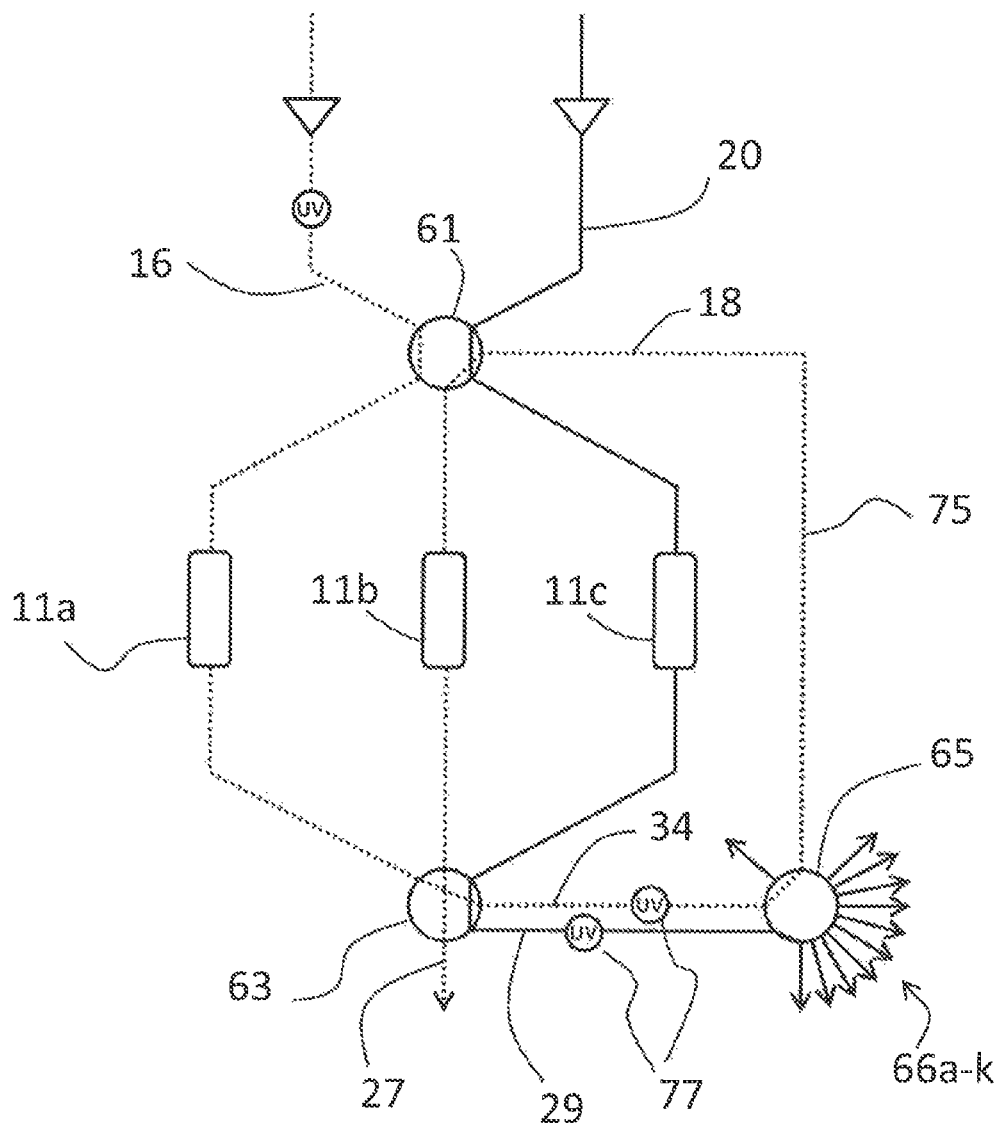
FIG. 2a shows schematically a chromatography system with three columns in which the rotary valve of the invention can be used.
Figure 2B:
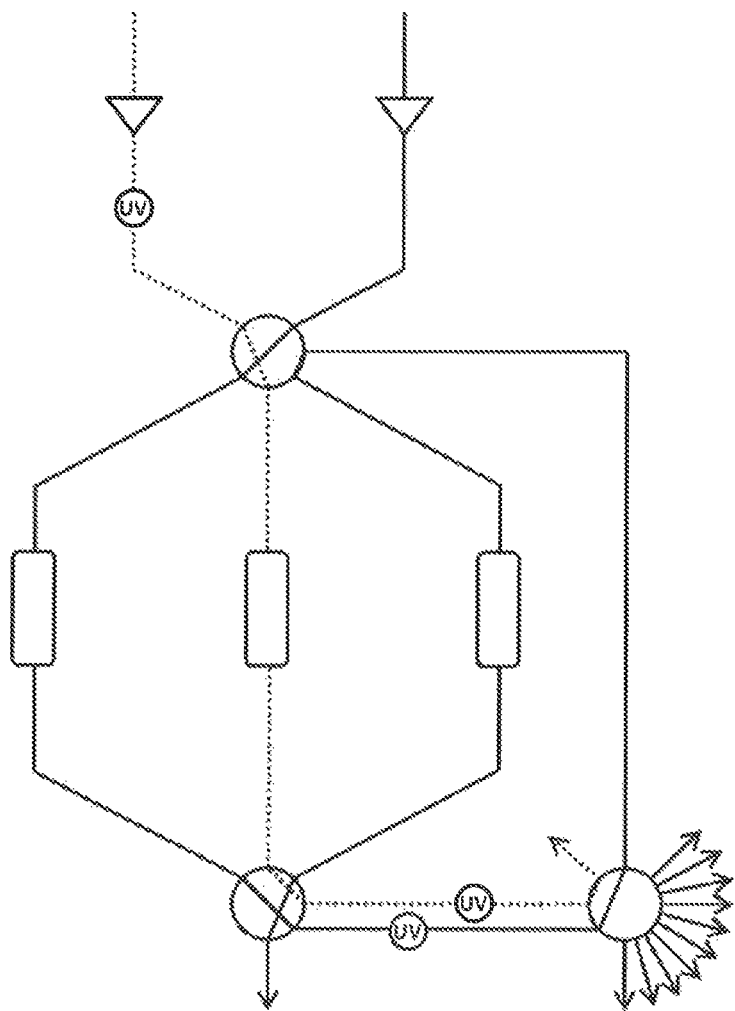
FIG. 2b shows schematically the chromatography system of FIG. 2a but in another step of the process.
Figure 2C:
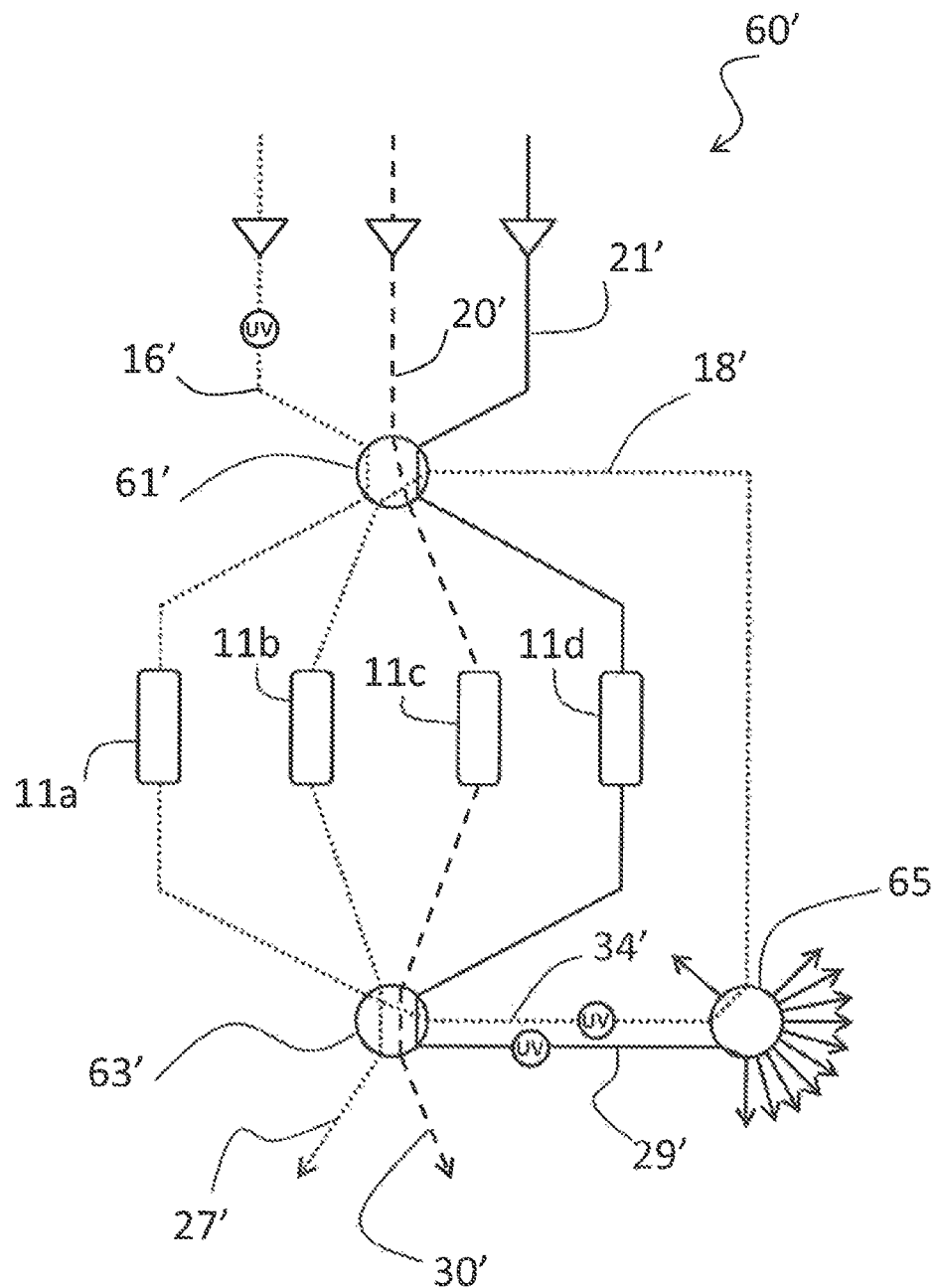
FIG. 2c shows schematically a chromatography system with four columns in which the rotary valve of the invention can be used.

FIG. 2a shows schematically a chromatography system 60 in which a rotary valve 65, also called a recirculation rotary valve, according to the invention can be provided. In this embodiment three columns 11a, 11b, 11c are connected in a simulated moving bed system. However, the number of columns can be varied. The rotary valve 65 according to the invention will not be any different with another number of columns connected in the system. In FIG. 2c a similar system comprising four columns is shown. A simulated moving bed system, also called a SMB system is a type of continuous chromatography where a number of chromatography columns are used in parallel and over and over again in a continuous process such that when one column for example is loaded with sample to be separated another column is eluted and another is washed and the process steps are shifted between the columns. One type of SMB is also called periodic counter current, pcc. The type of continuous chromatography described hereafter could be classified as pcc. A column inlet rotary valve 61 is connected to the inlets of the columns in the system. This column inlet rotary valve 61 is connected to the inlets of all the columns in the system and furthermore to a first inflow 16 (in this embodiment representing feed), a second inflow 18 (in this embodiment representing recirculation) and a third inflow 20 (in this embodiment representing wash, elution and regeneration buffer). A column outlet rotary valve 63 is connected to the outlets of all the columns in the system and furthermore to a first outflow 34 (in this embodiment representing feed waste or recirculation outlet), a second outflow 27 (in this embodiment representing recirculation waste outlet) and a third outflow 29 (in this embodiment representing elution, regeneration or recirculation outlet). A recirculation flow path 75 is provided between the column inlet rotary valve 61 and the column outlet rotary valve 63. All recirculation from the outlet of one column to the inlet of another column in the simulated moving bed chromatography system will be transferred through this recirculation flow path 75. A possible design of the column inlet rotary valve 61 and the column outlet rotary valve 63 is shown in our co-pending Swedish patent application SE 1351525-9. A recirculation rotary valve 65 according to the present invention is provided in the recirculation flow path 75. The recirculation rotary valve 65 is further connected to the third outflow 29 and to an optional number of outlets 66*a-k* used for sample fractionation or waste. According to the invention the feed outlet from a primary load column could be recirculated through the recirculation flow path 75 and the recirculation rotary valve 65 to a secondary load column while another column is eluted and the elution fractions are collected in one or more of the wanted outlets 66*a-k* from the recirculation rotary valve 65. The recirculation rotary valve 65 according to the invention further makes it possible to recirculate a wash fluid from one of the column outlets to another of the column inlets while the outlet from the primary feed column during this period is directed through the recirculation rotary valve 65 to a waste outlet. This is shown in FIG. 2*b*. In the beginning of the feed application to a primary load column all sample will be bound in the primary load column and the outlet can without risk of losing any sample be directed to waste while at the same time a wash fluid from another column instead is directed for recirculation to the secondary load column for binding of any possible sample washed out in the wash step. The recirculation rotary valve 65 is after this controlled back to feed recirculation as shown in FIG. 2*a* before any of the sample fed to the primary load column possibly could come through without binding.

A detector 77 is provided in the recirculation flow path 75. In this embodiment one detector 77 is provided in the first outflow 34 between the outlet rotary valve 63 and the recirculation rotary valve 65 and one detector 77 is provided in the third outflow 29 between the outlet rotary valve 63 and the recirculation rotary valve 65. This detector 77 is adapted to detect an effluent signal being representative of the composition of the fluid flowing through the detector. In one embodiment the detector is a UV detector, i.e. measuring the UV absorbance of the sample. Other possible types of detectors are measuring pH, conductivity, light scattering, fluorescence, IR or visible light. This definition of detector will be the same throughout the description.

A schedule for a simulated moving bed method (also called pcc) with feed and wash recirculation could in one embodiment of the invention be that if the feed is directed to the first column 11*a* then the outflow from the first column 11*a* should be directed to the inlet of the second column 11*b*. The second column 11*b* hereby serves as a secondary load column and the first column serves as a primary load column. When the first column is fully loaded, which could be measured by for example UV or time, the feed is instead directed directly to the second column 11*b* (hereby serving as primary load column). At the same time the first column 11*a* is washed and the outlet of the first column 11*a* is then recirculated to the inlet of the third column 11*c* while the outlet of the second column now serving as primary load column is directed to waste through the recirculation rotary valve 65. After the wash step the first column 11*a* is eluted. And the elution outlet from the first column 11*a* is then directed to any one of the outlets from the recirculation rotary valve 66*a-k* while at the same time the outlet from the second column 11*b* now is recirculated to the third column 11*c*. The last step in the continuous PCC process with three columns is when the third column 11*c* serves as primary load column. First wash is recirculated from the second column 11*b* to the first column 11*a* and then when the wash is ready and the second column is eluted the first column 11*a* serves as secondary load column and receives feed recirculation from the third column 11*c*. The benefit with a feed and wash recirculation is that the risk of losing any possible unbound sample is decreased and therefore the amount of sample provided to the column in the feed can be much higher than in normal chromatography. If there is any unbound feed left in the feed liquid after having passed the primary load column it will have another chance to bind in the secondary load column. This process is recycled. The rotary valves are controlled from a control system such that these above described flows are provided.

In FIG. 2*c* a chromatography system 60' is shown in which a rotary valve 65 according to the invention can be used. In this chromatography system 60' four columns 11*a*, 11*b*, 11*c*, 11*d* are connected instead of three. No change is required for the recirculation rotary valve 65. The difference in the system is only that an inlet rotary valve 61' is connected to the inlets of the four columns and to four inflows, a first inflow 16' representing feed, a second inflow 18' representing recirculation, a third inflow 20' representing regeneration buffer and a fourth inflow 21' representing wash and elution buffer. An outlet rotary valve 63' is connected to the outlets of the four columns and to four outflows, a first outflow 34' representing feed waste or recirculation, a second outflow 27' representing recirculation waste outlet, a third outflow 30' representing regeneration and a fourth outflow 29' representing elution or recirculation.

Figure 3A:
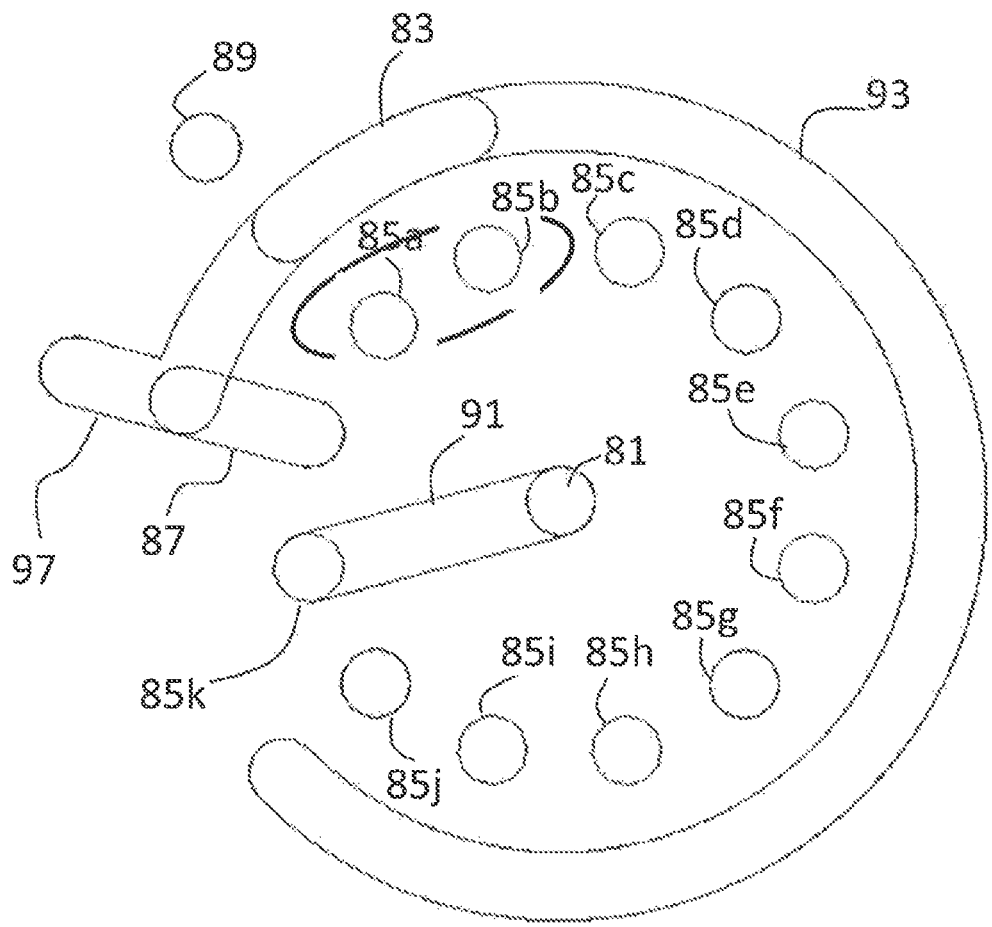
FIGS. 3a, 3b and 3c show a rotary valve according to one embodiment of the invention that can be used in the chromatography system of FIGS. 2a and 2b.
Figure 3B:
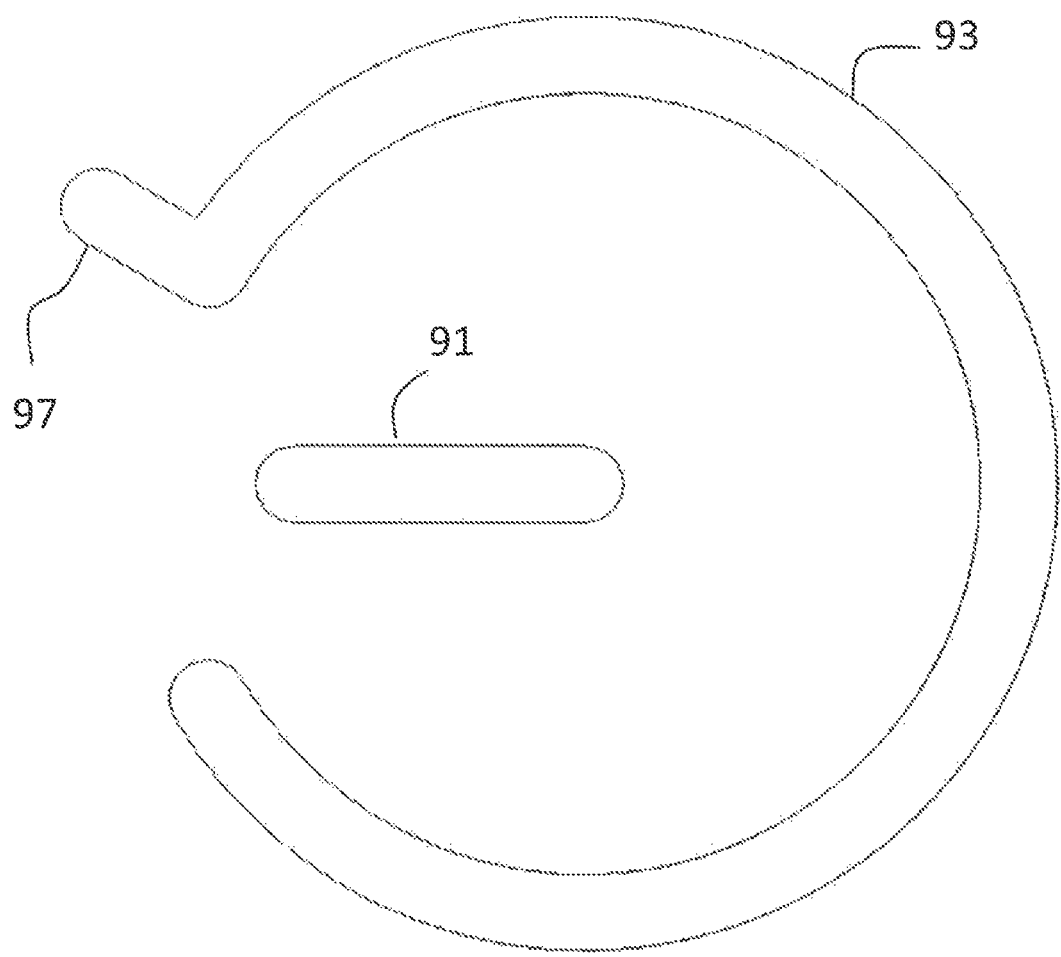
Figure 3C:
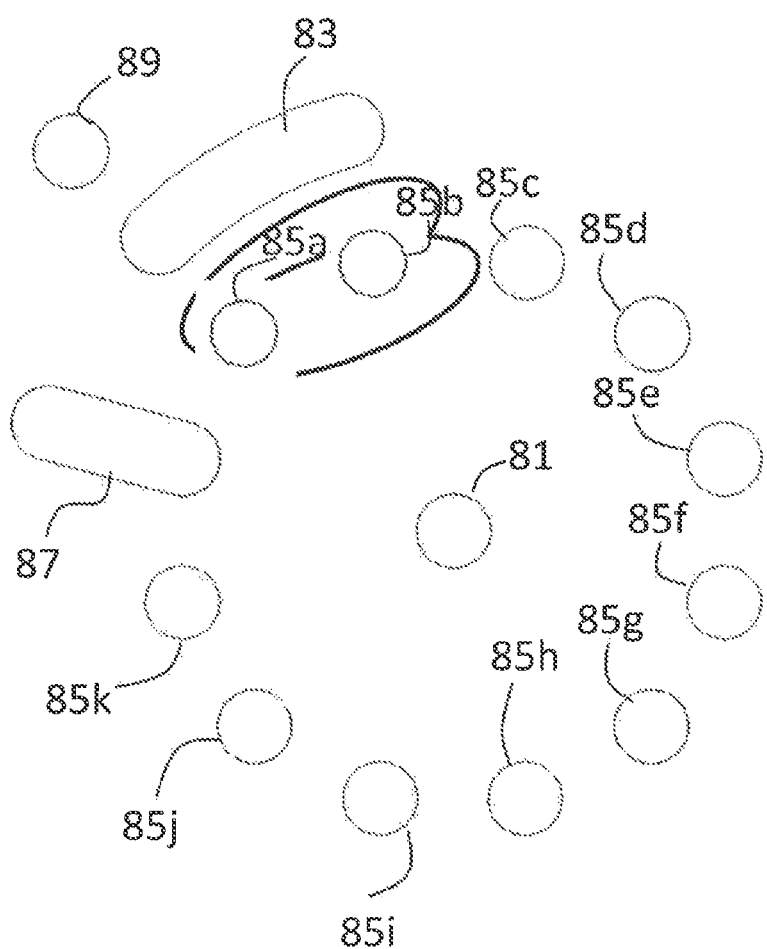
Figure 4:
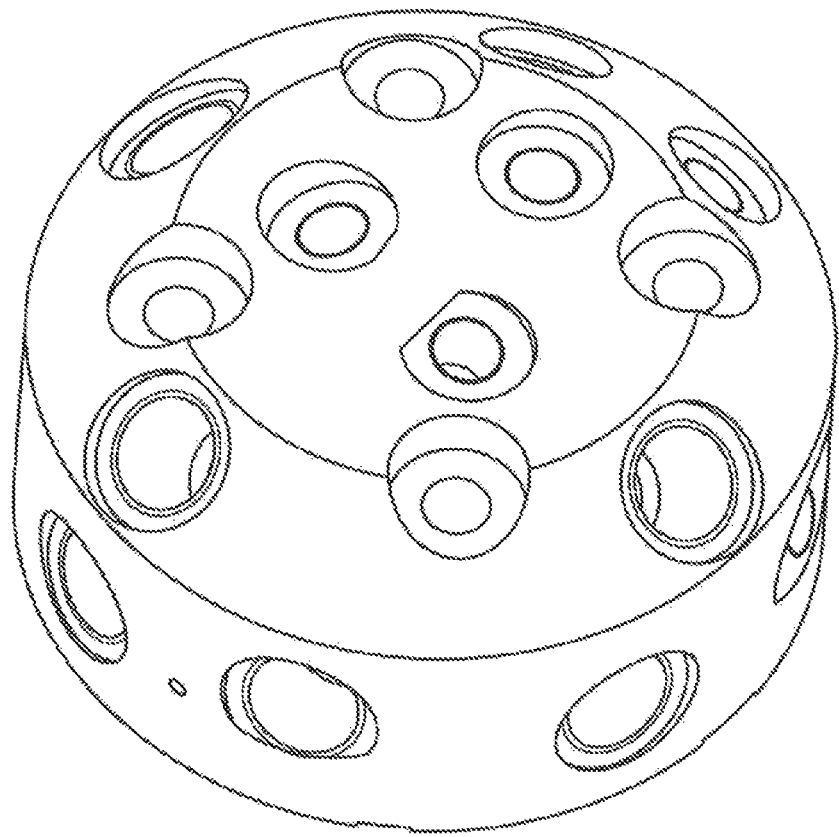
FIG. 4 shows connection ports on the outside of a rotary valve according to one embodiment of the invention.

FIGS. 3*a*-3*c* show a possible design of a recirculation rotary valve 65 that can be used in a chromatography system as shown in FIGS. 2*a* and 2*b*. A rotary valve comprises a stator with an inner stator face, and a rotor with an inner rotor face arranged in sealing contact with the inner stator face. The rotor is rotatably movable to a plurality of rotor positions about a rotational axis relative to the inner stator face. The stator comprises a plurality of connection ports each being in fluidic contact with a corresponding valve orifice at the inner stator face and the rotor comprises two or more interconnection paths for selective fluidic interconnection of said valve orifices with respect to the rotor position. In FIG. 3*a* the valve orifices on the inner stator face and the interconnecting paths on the rotor are shown in the same view. In FIG. 3*b* only the interconnecting paths on the rotor are shown and in FIG. 3*c* only the valve orifices are shown. In FIG. 4 connection ports on the outside of a stator is shown. However, these connection ports can be positioned in any wanted way. This is only one of many possible examples. In this embodiment of the recirculation rotary valve used in FIGS. 2*a* and 2*b* the stator comprises a first inlet orifice 81 in the center of the rotary valve and a second inlet orifice 83 at a radial distance R from the center of the rotary valve. In this embodiment the second inlet orifice 83 is an elongated orifice around a part of a circle around the first inlet orifice 81. This elongate design allows the proper connections to be provided. See further in the FIGS. 5*a* and 5*b* where two other rotational positions of the rotary valve are shown. The stator comprises further at least two, but in this shown embodiment 11 first outlet orifices 85*a,b,c,d,e, f,g,h,i,j,k* positioned around a circle with the first inlet orifice 81 in the center and with a radius different than R. In this example the radius is smaller than R but it could also be a larger radius than R. Furthermore, one second outlet orifice 87 is provided on the stator with a somewhat elongated form provided at the distance R from the first inlet orifice 81 but separate from the second inlet orifice 83 and reaching in to the circle on which the first outlet orifices 85a-k are provided. Finally, one third outlet orifice 89 is provided close to the second inlet orifice 83 but at a radial distance from the first inlet orifice 81 larger than R (however smaller than R if the first outlet orifices are provided on a radius larger than R). All of the stator orifices are in fluidic contact with a corresponding connection port of the stator. In the example shown in FIGS. 2a and 2b the third outflow 29 is connected to the first inlet orifice 81 and the first outflow 34 is connected to the second inlet orifice 83. Furthermore, the second outlet orifice 87 is connected to the second inflow 18. The first and third outlet orifices 85a-k and 89 are outlets from the system. The rotor comprises a first interconnection path 91 as a groove or as a drilled path within the rotor with its first end positioned at the valve center position of the first inlet orifice 81 and reaching out to the circle on which the first outlet orifices 85a-k are provided. A second interconnection path 93 is provided in the rotor as a groove with a partly circular design. The circular part of the second interconnection path 93 is provided at the radial distance R, i.e. the same radial distance as the second inlet orifice 83. However, the circle is not complete, there is one opening 95 enough for avoiding connection with the second outlet orifice 87 in one of the rotational positions of the rotary valve. This rotational position is when the rotor position shown in FIG. 3a is rotated one step clock wise (also shown in FIG. 5a). Hereby also the first inlet orifice 81 is connected through the first interconnection path 91 to the second outlet orifice 87. The second interconnection path 93 further comprises one protruding part 97 reaching out to the radial distance where the third outlet orifice 89 is provided on the stator (or into if the third outlet orifice is provided on a smaller radius than R).

Hereby there is one rotor position (shown in FIG. 5a) of the rotary valve where the first inlet orifice 81 is connected to the second outlet orifice 87 through the first interconnection path 91 and the second inlet orifice 83 is connected to the third outlet orifice 89 through the second interconnection path 93. This is the situation shown in FIG. 2b where elution/wash is directed for recirculation and primary feed outlet is directed to waste. All the other rotor positions of the rotary valve will direct the second inlet orifice 83 to the second outlet orifice 87 through the second interconnection path 93 and the first inlet orifice 81 to any of the first outlet orifices 85a-k (one for each rotary position) through the first interconnection path 91. This is the situation shown in FIG. 2a where the feed outlet from the primary feed column is directed for recirculation to a secondary feed column and the elution outlet from the column being eluted is directed through the recirculation rotary valve to any of the elution outlets 66a-k.

Figure 5A:
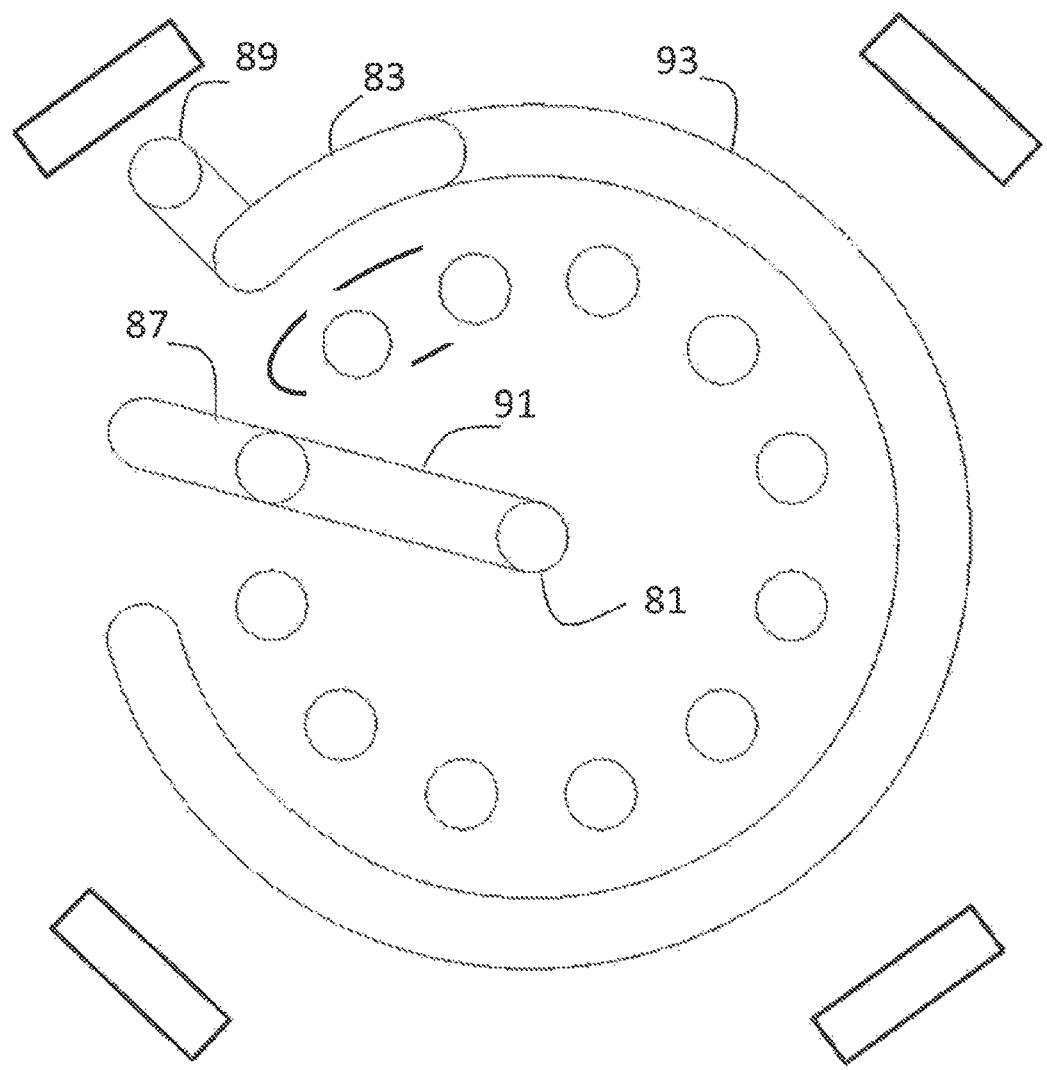
FIGS. 5a and 5b show two different rotary positions of the rotary valve of FIG. 3.
Figure 5B:
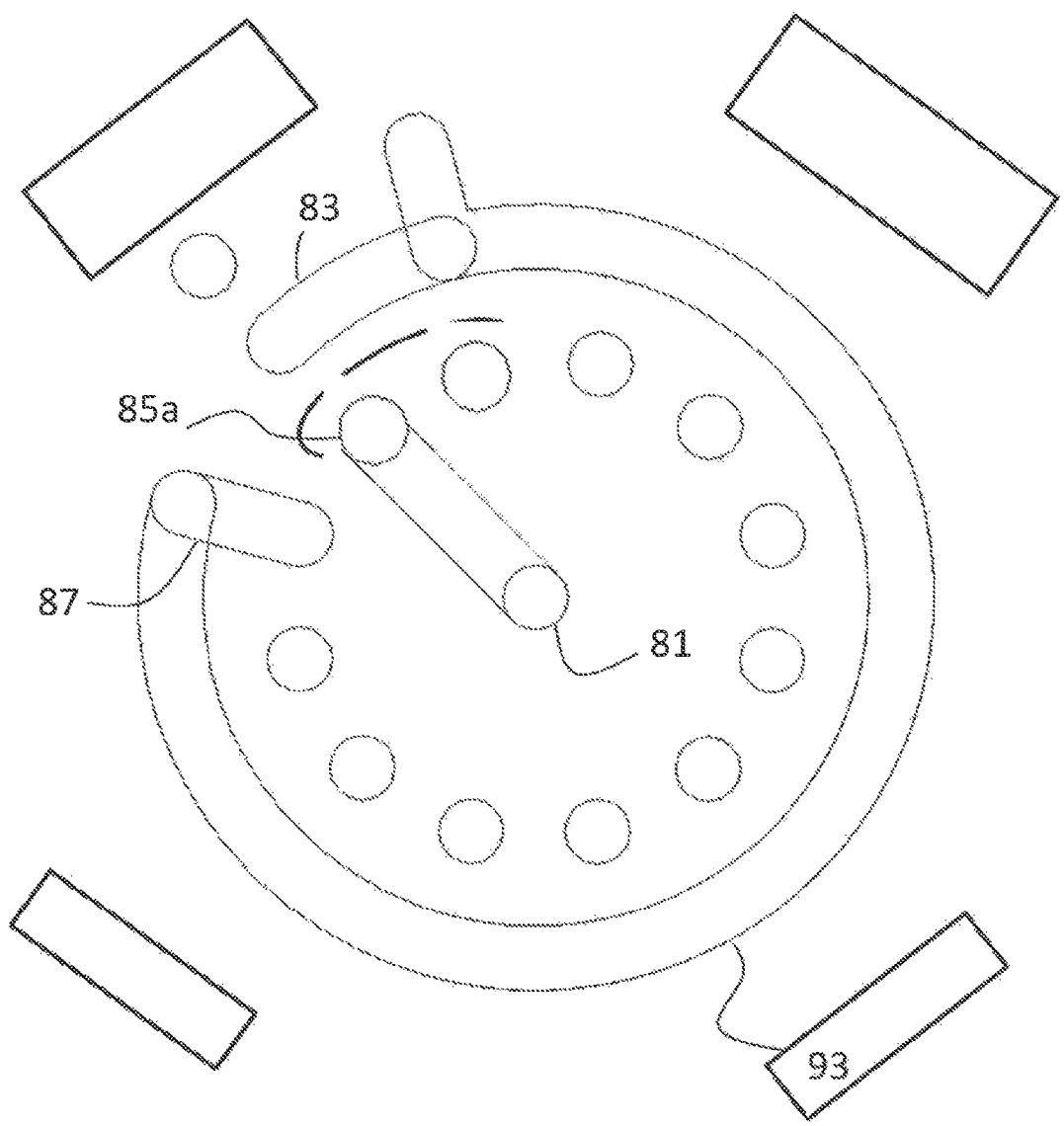

Two more rotational positions of the rotary valve are shown in FIGS. 5a and 5b. In FIG. 5a the first inlet orifice 81 is connected through the first interconnecting path 91 to the second outlet orifice 87 while the second inlet orifice 83 is connected through the second interconnecting path 93 to the third outlet orifice 89. In FIG. 5b the first inlet orifice 81 is connected to the first outlet orifice 85a while the second inlet orifice 83 is connected to the second outlet orifice 87 through the second interconnection path 93.

The invention claimed is:

1. A rotary valve comprising a stator with an inner stator face, and a rotor with an inner rotor face arranged in sealing contact with the inner stator face, the rotor is rotatably movable to a plurality of rotor positions about a rotational axis relative to the inner stator face, the stator comprises a plurality of connection ports each being in fluid communication with a corresponding valve orifice at the inner stator face and the rotor comprises two or more rotor interconnection paths for selective fluid interconnections of said valve orifices at preselected rotor positions, wherein
   the stator comprises a first inlet orifice and a second inlet orifice, at least two first outlet orifices, a second outlet orifice and a third outlet orifice, and wherein
   the rotor interconnection paths are arranged to:
      in at least one rotary position connect the first inlet orifice to the second outlet orifice and the second inlet orifice to the third outlet orifice, and
      in at least two other rotary positions, connect the first inlet orifice with any one of
   the at least two first outlet orifices at the same time as the second inlet orifice is connected to the second outlet orifice,
      the rotary valve being connected in a recirculation path to one or more outflows of a column outlet rotary valve of a chromatography system, wherein a first outflow of the column outlet rotary valve is connected to the second inlet orifice in the rotary valve and a third outflow from the column rotary valve is connected to the first inlet orifice of the rotary valve and a second inflow of the chromatography system is connected to the second outlet orifice of the rotary valve.

2. A rotary valve according to claim 1, wherein at least one of the rotor interconnection paths is a partly arcuate groove.

3. A rotary valve according to claim 2, wherein the first inlet orifice is provided in the centre of the rotary valve and the at least two first outlet orifices are provided in an arc about the first inlet orifice, and the second inlet orifice is provided at a radial distance R from the first inlet orifice that is different to the radial distance at which the first outlet orifices are provided, and a first interconnection path is provided such that it can connect the first inlet orifice with any one of the first outlet orifices and a second interconnection path is arcuate with an opening at the same radial distance from the first inlet orifice as the second inlet orifice.

4. A chromatography system comprising at least three chromatography columns and the rotary valve of claim 1 said system further comprising:
   the column inlet rotary valve being connected to the inlets of at least three columns in the system and to at least three inflows and
   the column outlet rotary valve being connected to the outlets of at least three columns in the system and to at least three outflows.

5. A chromatography system according to claim 1, wherein the feed recirculation flow path comprises a detector.

6. The rotary valve of claim 1, wherein:
   the second inlet orifice is an elongated orifice around a part of a circle around the first inlet orifice;
   the at least two first outlet orifices are positioned around the circle with the first inlet orifice in a center thereof;
   the second outlet orifice is provided on the stator in an elongated form at a distance from the first inlet orifice but separate from the second inlet orifice; and the third inlet orifice is adjacent to the second inlet orifice but a predetermined distance away from the first inlet orifice.

7. A method in a simulated moving bed chromatography system comprising a recirculation flow path in which recirculation fluid from the outlet of one column to an inlet of another column is transferred, the method comprising:
- connecting a column inlet rotary valve to inlets of each column;
- connecting a column outlet rotary valve to outlets of each column;
- selecting which one of two flows in the chromatography system to be recirculated in the recirculation flow path
- transferring recirculation fluid from the outlet of one column to the inlet of the other column wherein the recirculation flow path is connected to the inlets and the outlets through the column inlet rotary valve and the column outlet rotary valve, and wherein a recirculation valve is connected in the recirculation flow path and to one or more outflows of the column outlet rotary valve.

8. A method according to claim 7, wherein the chromatography system further comprises
- at least one column inlet valve connected to the inlets of at least three columns in the system and to at least three inflows and
- at least one column outlet valve connected to the outlets of at least three columns in the system and to at least three outflows, and
- wherein the recirculation fluid from the outlet of one column is transferred to the inlet of another column via the recirculation flow path, wherein said recirculation flow path is connected to the inlets and outlets of the columns through the column inlet and column outlet valves, wherein said method comprises directing two of the outflows from the at least one column outlet valve through the recirculation flow path one at the time.

* * * * *